United States Patent [19]
Hazen

[11] Patent Number: 5,324,661
[45] Date of Patent: Jun. 28, 1994

[54] CHEMOTACTIC SELECTION OF POLLUTANT DEGRADING SOIL BACTERIA

[75] Inventor: Terry C. Hazen, Augusta, Ga.

[73] Assignee: The United States of America as represented by the United States Department of Energy, Washington, D.C.

[21] Appl. No.: 663,517

[22] Filed: Mar. 4, 1991

[51] Int. Cl.$^5$ .................. C12Q 1/04; C12Q 1/00; C12R 1/01
[52] U.S. Cl. .................... 435/262; 435/34; 435/39; 435/262.5; 435/264; 435/281; 435/821
[58] Field of Search .............. 435/262, 262.5, 34, 435/39, 264, 281, 821

[56] References Cited

U.S. PATENT DOCUMENTS

| | | | |
|---|---|---|---|
| 1,341,030 | 5/1920 | Wood | 435/252.1 |
| 1,494,435 | 5/1924 | Lipman | 71/10 |
| 1,515,016 | 11/1924 | Earp-Thomas | 435/252.1 |
| 1,891,750 | 12/1932 | Cornell | 435/252.1 |
| 4,647,533 | 3/1987 | Weller et al. | 435/29 |
| 5,143,827 | 9/1992 | Atlas et al. | 435/30 |
| 5,155,042 | 10/1992 | Lupton et al. | 435/262.5 |
| 5,160,488 | 11/1992 | Stillman | 435/262.5 |
| 5,200,343 | 4/1993 | Cole et al. | 435/262.5 |
| 5,238,842 | 8/1993 | Hannay et al. | 435/262.5 |

OTHER PUBLICATIONS

McCarty J of Hazardous Materials 28 (1991) pp. 1-11.
Fard et al Biotechnology & Bioengineering vol 37 pp. 661-672 Mar. 1991.

Primary Examiner—Michael G. Witshyn
Assistant Examiner—Jane Williams
Attorney, Agent, or Firm—Brian R. Tumm; Harold H. Dixon; William R. Moser

[57] ABSTRACT

A method for identifying soil microbial strains which may be bacterial degraders of pollutants comprising the steps of placing a concentration of a pollutant in a substantially closed container, placing the container in a sample of soil for a period of time ranging from one minute to several hours, retrieving the container, collecting the contents of the container, and microscopically determining the identity of the bacteria present. Different concentrations of the pollutant can be used to determine which bacteria respond to each concentration. The method can be used for characterizing a polluted site or for looking for naturally occurring biological degraders of the pollutant. Then bacteria identified as degraders of the pollutant and as chemotactically attracted to the pollutant are used to inoculate contaminated soil. To enhance the effect of the bacteria on the pollutant, nutrients are cyclicly provided to the bacteria then withheld to alternately build up the size of the bacterial colony or community and then allow it to degrade the pollutant.

7 Claims, 3 Drawing Sheets

*Fig. 1*

(graph: RESPONSE vs DECREASING CONCENTRATION, peak labeled 10)

*Fig. 2*

```
IDENTIFY              SELECT           FILL CAPILLARY
POLLUTANTS    →       SOIL       →     TUBES WITH
IN PLUME              SAMPLES          POLLUTANT
                                            ↓
ANALYZE              REMOVE            PLACE CAPILLARY
BACTERIAL     ←      CAPILLARY   ←     TUBES IN SOIL
CONTENT OF           TUBES             SAMPLES
CAPILLARY TUBES
    ↓
SELECT               CULTURE           INNOCULATE
BACTERIAL     →      SELECTED   --→    POLLUTANT
STRAINS              STRAINS           PLUME
                        ↓                  ↓
                     INNOCULATE        FEED
                     BIOFARM           BACTERIA
                        ↓                  ↑
STARVE               FEED              STARVE
BACTERIA      ←→     BACTERIA    →     BACTERIA
```

CHEMOTACTIC SELECTION OF POLLUTANT DEGRADING SOIL BACTERIA

BACKGROUND OF THE INVENTION

1. Field of the Invention

The present invention relates to remediation of contaminated soil, particularly remediation by bacteria, and more particularly the use of microbes for the degradation of chemical pollutants. The United States Government has rights in the present invention pursuant to Contract No. DE-AC09-89SR18035 between the U.S. Department of Energy and Westinghouse Savannah River Company.

2. Discussion of the Background

Use of microbes in industrial processes and pollution control continues to increase. Microbes are efficient and economical transformers of chemical compounds and intense effort is underway to find or engineer microbes suitable for various industrial purposes.

It was thought that certain types of compounds would not lend themselves to microbial degradation, compounds such as xenobiotic or synthetic chemicals, since these chemicals are usually toxic, do not occur naturally in the environment, and become recalcitrant when placed in a natural environment. However, research has shown that these, too, can be degraded. The range of applications for microbial degradation is thus greatly increased. In the treatment of effluents from sewage treatment plants and other industrial processes, microbial transformation of compounds is now common practice.

The major drawbacks in the utilization of microbes in remediation of contaminated groundwater and soils are the small size and sparse distribution of in situ microbial populations. Although found throughout the subsurface even to great depths, the concentration of microbes usually available for remediation of a plume of contaminants is generally low.

Stimulating microbes to degrade the contaminants is a possible solution to the drawbacks of small population numbers and sparse distribution. Generally, nutrients are injected or infused into the soil to provide nutrients that have become limiting to the microbes and thus promote the growth of microbial degraders. Many of these nutrients will stimulate the growth of both degraders and nondegraders. Identifying those microbes most effective at breaking down a given contaminant is a more efficient approach to remediation. Once the correct microbes are identified, nutrients optimal to those microbes can be supplied to enhance population growth. The identifying process should be as simple as possible in order to save time. Conventional methods of bioremediation site characterization, monitoring and control use culturing techniques which require days or weeks to incubate a colony large enough to visualize. Culturing is inaccurate because it is not specific and does not allow all environmentally active microbes to grow.

Microbes move in the ground sometimes randomly, sometimes with the flow of ground water and sometimes in response to taxis effects. A particular type of taxis is chemotaxis, defined as the movement of microorganisms toward or away from a chemical. Chemotaxis is positive or negative depending on whether it is toward or away from the chemical, respectively. Through chemotaxis, microbes seek optimum surroundings, such as those having nutrients, and avoid unfavorable ones, such as those without nutrients or with toxins. The movement is characterized by two actions, one called "runs" and one called "twiddles". When the organism runs, it swims steadily in a gently curved path. When it twiddles, it stops and jiggles in place. After a twiddle, the organism runs off again in a new direction. A twiddle is a random event, and following a twiddle, the direction for the next run is also random. When a chemical gradient is added, the random movements become biased. As the organism experiences higher concentrations of an attractant, the runs become longer and the twiddles become less frequent.

Although chemotaxis is not completely understood, it is believed that a set of proteins, called chemoreceptors, exist in the cell wall or membrane of the microorganisms and are specific for groups of closely-related compounds. A second set of proteins, methyl-accepting chemotaxis proteins (MCP), translates chemotactic signals to the flagellar motor of the microorganism. Methylation catalyzes the MCP to produce a chemical mediator that diffuses the flagellar motor so that it rotates in the same direction, thereby lengthening runs and decreasing twiddles of the microorganism's motion until the microorganism can no longer sense a concentration gradient in the chemical substance. At some point the microorganism's receptors saturate and no further increase in the substance will increase the chemotacic response.

The chemotaxis of a microbe can be used to advantage when determining which microbe will degrade a given pollutant.

SUMMARY OF THE INVENTION

In accordance with its major aspects, the present invention is a method for identifying microbial strains in soil for bacterial degradation of pollutants. Microbial strains that are attracted to a given pollutant or pathogen are identified by placing an amount of the pollutant or pathogen within a container, such as a capillary tube, placing the container in a sample of soil either in situ or in a laboratory, leaving the container in the soil for relatively short period of time, retrieving the container, collecting a portion of the contents of the container, and analyzing the portion either microscopically or by culturing on media to determine the presence and identify of microbes that have been attracted to the pollutant. The microscopic analysis is performed without first culturing the sample. Microbes that are chemotactically attracted to the chemical pollutant will be found in the retrieved sample. Preferably, a second, control tube is placed in the soil near the first, the second filled with water or diluent, so that random motility can be discounted. Bacteria attracted to the pollutant-containing capillary tube by the chemotaxis response may be degraders of the pollutant. The concentration of the pollutant may be varied over several orders of magnitude to identify which bacteria are attracted to which concentration and what the critical concentration is for each type of bacteria.

The present invention helps to optimize the various known bioremediation methods. The appropriate microbe for a given bioremediation procedure may be quickly determined by the present invention and then brought to bear on the site to be remediated. The chemotactic response of a given microbe to the concentration of pollutant within the container is an indicator of that microbe's affinity to the pollutant. However, not all microbes chemotactically attracted to a certain concentration of pollutant are degraders of that pollutant.

The present method is useful in the characterization and monitoring of a polluted site during its degradation by microbes. It may also be used to identify new microbial strains capable of degrading pollutants, separating degraders from other bacteria, selecting more responsive degraders from less responsive, as well as identifying those degraders tolerant or more responsive to different concentrations of chemical pollutants or pathogens. Alternating nutrient injection with nutrient withholding at the site where the microbes are infused will alternatingly enhance the health of the microbial colony and then effectively starve the colony so that it has only the pollutant to degrade, for lack of nutrients, and thereby remediates the soil.

A feature of the present invention is the requirement of only simple laboratory supplies and techniques. An advantage of this feature is the relative ease with which determination can be made and the minimal cost required. The present invention, in a preferred embodiment, utilizes capillary tubes as containers for the pollutant.

Another feature of the present invention is the length of time needed from start through identification to identify bacteria chemotactically attracted to the pollutant. The container of chemical pollutant is left in the soil for one minute to several hours before being retrieved. Microscopic analysis takes place directly, without culturing the sample from the container. An obvious advantage of this feature is the savings in time and avoidance of specialized media needed for identification of the bacteria attracted to the pollutant. Related to this advantage is the simplicity of making the determination. Because the numbers of bacteria drawn into the tube chemotactically is much larger than the naturally occurring population density, the conventional step of culturing the sample is eliminated and the time associated with culturing is saved. Furthermore, since culturing of bacteria is not always successful, bacteria that would otherwise be lost as a result of unsuccessful culturing will be found and might be used successfully for remediation.

Yet another feature of the present invention is the need for only a portion of the sample from the container for assaying, leaving an unused portion of the microbe sample within the container. This remaining portion is available for immediate use in culturing if the microbe is determined to be a degrader of the pollutant or as a reference colony for archival purposes.

Another feature of the present invention is that this technique will also act as a selective enrichment technique for isolating degraders. This would also save time by avoiding elaborate media and culturing in order to determine degrader numbers and identity.

Other features and advantages of the present invention will become apparent to those skilled in the art of chemotactic harvesting of soil bacteria from a careful reading of the following description and the accompanying drawings which illustrate an embodiment of the invention.

BRIEF DESCRIPTION OF THE DRAWINGS

FIG. 1 is a graph showing the normal chemotaxis response of microorganisms to nutrients;

FIG. 2 is a schematic diagram of an embodiment of the present invention;

DETAILED DESCRIPTION OF PREFERRED EMBODIMENTS

The most appropriate microbes for the remediation of a contaminated site may be site specific. These microbes are distributed, generally, in the area and many may be degraders of the pollutant. Some microbes may be chemotactically attracted to the pollutant as well. Some of these may also be degraders. The present invention identifies and uses such microbes: chemotactically attracted biodegraders of the pollutant of interest.

FIG. 1 depicts the usual chemotaxis response of microorganisms to nutrients. As might be expected, the response to nutrients is positive with increasing strength to higher concentrations of the nutrients. Beyond a critical concentration 10, however, the chemoreceptors of the microorganisms appear to saturate and the response becomes less, even though the concentration is higher.

The present invention takes advantage of this chemotactic response to detect microbes which chemotactically respond to pollutants. Often, a polluted site is contaminated with more than one pollutant. Not all pollutants cause a positive chemotaxis in any given microbe. Indeed, as is evident from FIG. 1, the concentration of a given pollutant has an effect on the chemotaxis response of an attracted microbe. In order to take advantage of the chemotaxis response of a variety of the microbes in the soil, several concentrations of the pollutant may be made available to the variety so that the optimum concentration for each microbe may be determined.

As illustrated in FIG. 2, a pollutant is identified; a sample of the soil containing the pollutant is selected and either left in situ or taken to a laboratory; a container, preferably a capillary tube, is filled with an amount of the pollutant at a known concentration; the tube is placed in the soil sample and retrieved after a time which can range from one minute to several hours; a portion of the contents of the container are then analyzed for bacterial content. The bacterial strain of interest, which may be the microbial biodegrader with the most positive chemotaxis response to the pollutant at that concentration, can be cultured and then either inoculated into the plume of pollution or inoculated into the soil ahead of an advancing plume. To improve the degradation abilities of the microbe, nutrients may be infused into the site for limited periods of time to alternately feed and then starve the microbial community. Nutrients will build up the community; withholding nutrients forces the robust community to degrade the pollutant but, when the community is depleted, the nutrients must be resupplied. If nutrients are always available, the microbes will degrade them rather than the pollutant.

Figure 3:
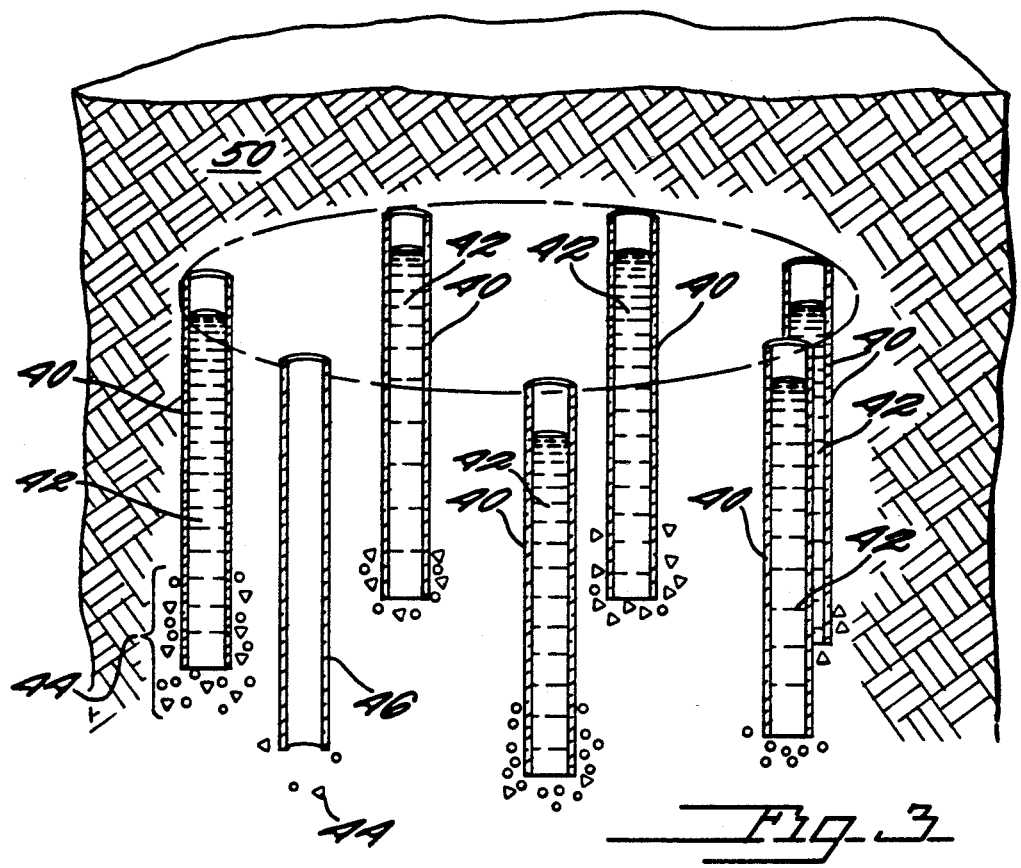
FIG. 3 is an embodiment of the present invention showing a cluster of capillary tubes having different concentrations of pollutant.

FIG. 3 depicts an embodiment of the present invention in which several capillary tubes 40, each with a different concentration of pollutant 42, are bundled together in the soil 50. The tubes are shown placed in the soil vertically, however it will be clear that the tubes could also be placed horizontally or at any given angle within the soil. Capillary action will prevent the leaking of the contents regardless of the position yet the tubes will admit the migrating microbes. Each tube 40 attracts microbes 44 to a greater or lesser extent because of the different concentration of pollutant 42 therein. In the bundle, at least one tube 46 is devoid of pollutant 42 to serve as a control so that random motility of the microbes 44 can be discounted.

An illustrative example of the use of the present invention is the identification of microbes to remediate a site polluted with several different chemical pollutants. Since a given microbe may be more or less chemotactically attracted to various concentrations of a given pollutant, a different concentration of the pollutant is placed in each capillary tube of a cluster or bundle of tubes. This procedure is repeated with each of the known pollutants to ensure selection of the most appropriate microbe for a given concentration of a given pollutant. The concentrations of a pollutant may be bundled together or several different concentrations of different pollutants may be grouped in a bundle. These bundles are then placed in the soil and later retrieved for assaying as described above.

A second illustrative example relates to site characterization. Various soil samples are selected from several locations within the site and capillary tube bundles containing a range of concentrations of the pollutants are placed therein. The concentration is selected, preferably, to range over several orders of magnitude above and below the nominal concentration of the pollutant at that site. After a length of time, the tube is retrieved. Assay determines the relative chemotaxis response of microbes into one or more capillary tubes, indicating the preferred microbe for each concentration of pollutant. This characterization is especially helpful since most contaminated sites have varying concentrations of pollutants.

Figure 4:
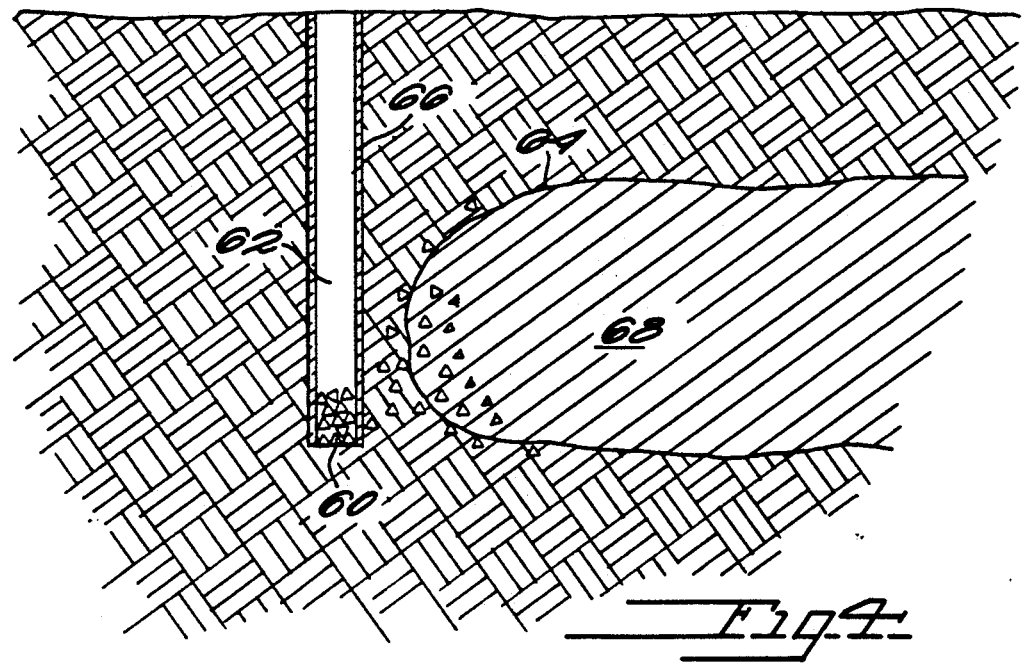
FIG. 4 is an illustration of an embodiment of the present invention as applied to remediate a plume of contamination.

FIG. 4 depicts the placement of the most appropriate microbe 60 into a porous well 62 placed adjacent the remediation site 64. Microbe 60 migrates by chemotaxis through the wall 66 of well 62 to the pollutant 68. Several wells may be drilled around and into the remediation site so that degrading microbes may form a boundary at the periphery of the plume of pollution as well as attack the pollutant from within.

Illustrative again of this embodiment is a situation in which the pollutant seeps into surrounding soil, in this case in one direction only. Determination of the most appropriate microbe for the concentration of pollutant at the leading edge of the plume is made by the method disclosed above. By inoculating the soil with a colony of microbes selected for the concentration of pollutant at the leading edge of the plume, the movement of the pollutant that is seeping into surrounding soil is stopped. Other microbes selected for different concentrations at other locations within the plume of contamination are infused into those locations and the soil is remediated there. Additionally, an appropriate microbe can be infused around the periphery of a given site to create a microbial barrier beyond which pollutant cannot extend. Biodegradation can be effected at any location by inoculating the soil with the appropriate microbes.

Figure 5A:
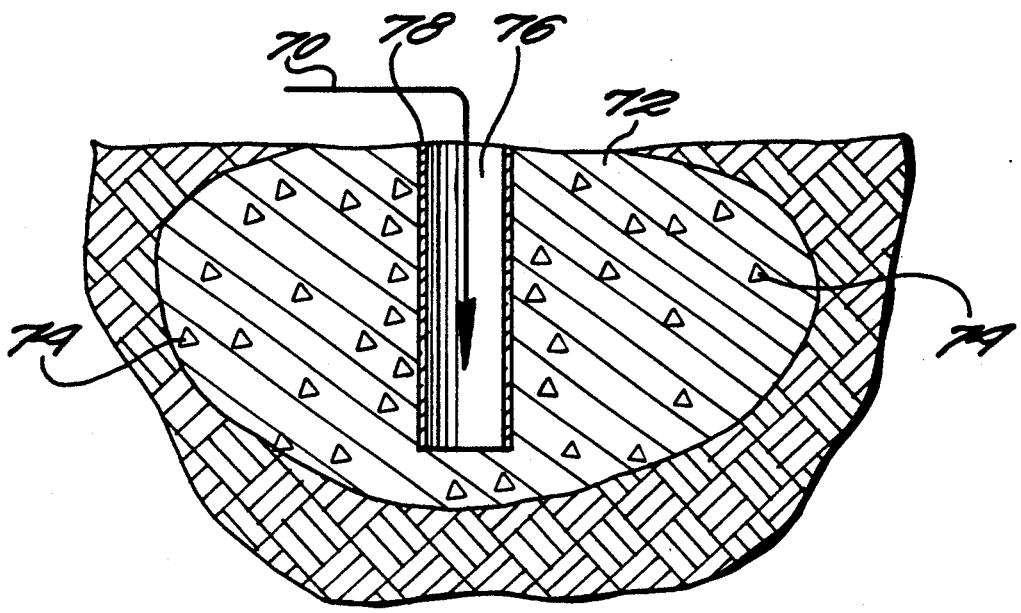
FIG. 5a is an illustration of an embodiment of the present invention showing nutrients being supplied to the microbes to enhance the population concentration.
Figure 5B:
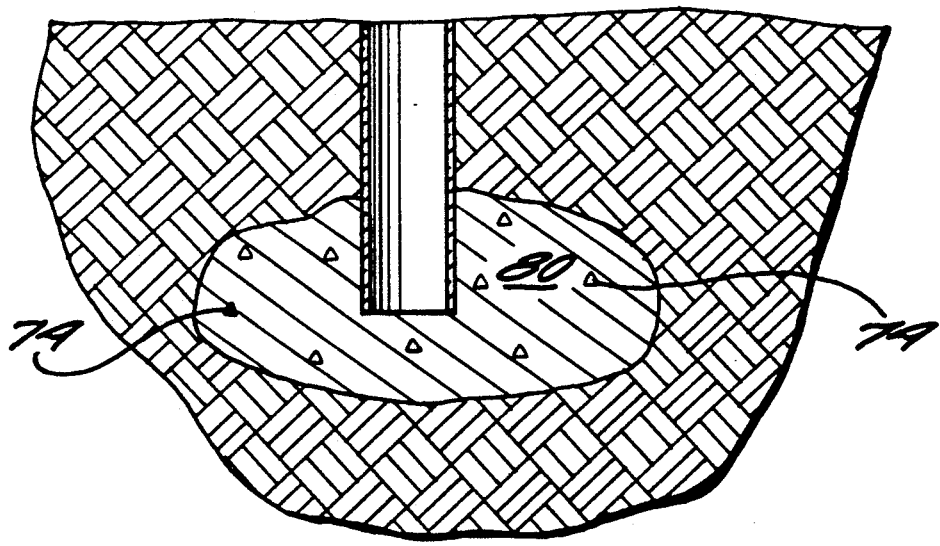
FIG. 5b is an illustration of the embodiment of FIG. 5a with the nutrients no longer supplied and the microbes degrading the pollutant.

FIG. 5a depicts nutrients 70 being infused into the soil of a site 72 containing microbes 74. One method of infusion is through a well 76 with porous or permeable walls 78. As microbes 74 increase in number or population density due to the supply of nutrients 70, the nutrients 70 are withdrawn, as depicted in FIG. 5b, so that microbes 74 attack and degrade pollutant 72 for lack of nutrients. The supply of nutrients are pulsed in this infusion-withdrawal cycle so that the microbial community alternates between a larger, healthier community followed by starvation of the community so that it attacks the pollutant in greater numbers when the nutrients are withdrawn. If nutrients are always available, the microbes will tend to degrade the nutrients first, then the pollutants.

A third example, illustrating cyclic feeding, is a situation in which a microbe is determined to be positively chemotactic to the pollutant yet exhibits only fortuitous metabolism. Fortuitous metabolism means degradation without nutritional benefit. In order to maintain the degradation process, periodic supply of nutrients is essential to sustain the microbial colony. By subsequently withdrawing the nutrients, the microbes are restricted to degrading the pollutant. When the colony is depleted to the point of inefficient remediation, more nutrients are infused to return the colony to an effective size. The withdrawal-infusion cycle is continued until the remediation is complete.

It will be apparent to those skilled in the art of bioremediation of groundwater pollution that other changes, additions and substitutions can be made without departing from the spirit and scope of the present invention, which is to be defined by the appended claims.

What is claimed is:

1. A method of remediation of soil contaminated with a pollutant, comprising the steps of:

selecting a bacterial strain chemotactically attracted to said pollutant by filling a container with a concentration of said pollutant, said container retaining said pollutant without substantial leakage while admitting bacterial strains chemotactically attracted to said pollutant, placing said container in said soil, leaving said container in said soil for a length of time, retrieving said container from said soil, and analyzing the contents of said container to identify said strains, said analysis performed without culturing said strains; and inoculating said soil proximate to said pollutant with the selected strain so that at least a portion of said selected strain bounds at least a portion of said soil, so that said selected strain will be attracted to said pollutant and will degrade said pollutant in said portion of said soil.

2. The method as recited in claim 1, further comprising the step of:

culturing said selected strain before inoculating said soil.

3. The method as recited in claim 1, further comprising the steps of:

supplying nutrients to the inoculated strain so that said strain population grows in size and density; and terminating the supply of nutrients so that said inoculated strain degrades said pollutant rather that said nutrients.

4. A method for containing a chemical pollutant plume in soil comprising the steps of:
   selecting a bacterial strain chemotactically attracted to said pollutant by
      placing a concentration of said pollutant within a container, said container retaining said pollutant without substantial leakage while admitting bacterial strains chemotactically attracted to said pollutant,
      placing said container in said soil,
      leaving said container in said soil for a length of time,
      retrieving said container from said soil, and
      analyzing the contents of said container to identify said strains, said analysis performed without culturing said strains; and
   inoculating said soil with the selected strain proximate to said pollutant so that at least a portion of said selected strain surrounds said plume, so that said selected strain is attracted to said pollutant whereby said pollutant is degraded and contained by said selected strain.

5. The method as recited in claim 4, further comprising the step of:
   culturing said selected strain before inoculating said soil.

6. The method as recited in claim 4, wherein said container is a bundle of capillary tubes and said length of time is at least one minute.

7. The method as recited in claim 4, further comprising the steps of:
   supplying nutrients to the inoculated strain so that said strain population grows in size and density; and
   terminating the supply of nutrients so that said inoculated strain degrades said pollutant rather than said nutrients.

* * * * *